United States Patent [19]

Dawson

[11] 4,272,920

[45] Jun. 16, 1981

[54] METHOD OF APPLYING HERBICIDE

[75] Inventor: Jean H. Dawson, Prosser, Wash.

[73] Assignee: The United States of America as represented by the Secretary of Agriculture, Washington, D.C.

[21] Appl. No.: 83,694

[22] Filed: Oct. 11, 1979

Related U.S. Application Data

[63] Continuation-in-part of Ser. No. 907,474, May 19, 1978, abandoned.

[51] Int. Cl.³ ........................... A01C 1/06; A01N 9/12
[52] U.S. Cl. ......................................... 47/58; 47/57.6; 71/100
[58] Field of Search ...................... 47/57.6, 58; 71/100

[56] References Cited

U.S. PATENT DOCUMENTS

| | | | |
|---|---|---|---|
| 2,502,809 | 4/1950 | Vogelsang | 47/57.6 |
| 3,749,566 | 7/1973 | Hoffmann | 47/57.6 X |
| 3,930,838 | 1/1976 | Pellegrini et al. | 47/57.6 X |
| 4,021,228 | 5/1977 | Arneklev et al. | 47/57.6 X |
| 4,070,389 | 1/1978 | Martin | 71/100 X |
| 4,079,545 | 3/1978 | Smith | 47/57.6 |
| 4,152,137 | 5/1979 | Martin | 47/57.6 X |

*Primary Examiner*—Robert E. Bagwill
*Attorney, Agent, or Firm*—M. Howard Silverstein; David G. McConnell

[57] ABSTRACT

A method of applying herbicide wherein the herbicide and crop seed are simultaneously introduced into soil in close proximity to one another. In a preferred embodiment of the invention crop seed is treated with herbicide and then is sown according to conventional techniques.

20 Claims, No Drawings

METHOD OF APPLYING HERBICIDE

CROSS-REFERENCE TO RELATED APPLICATIONS

This is a continuation-in-part of my co-pending application, Ser. No. 907,474, filed May 19, 1978, now abandoned.

BACKGROUND OF THE INVENTION

1. Field of the Invention

This invention relates to and has among its objects the provision of novel methods for applying herbicides to soil. Further objects of the invention will be evident from the following description wherein parts and percentages are by weight unless specified otherwise.

2. Description of the Prior Art

Natural and synthetic herebicides have been employed for some time in controlling the growth of undesirable plants, especially those on crop land. Herbicides are conventionally applied in a variety of ways depending on the type of herbicide used and the nature of growth to be controlled. One method of applying herbicides for selective control of weeds involves dispersing a herbicide formulation onto the soil surface before crop seed is planted. The treated soil is tilled, generally once or twice, to mix the herbicide therein. Then, the crop seed is sown. In another application technique liquid formulations of certain herbicides are sprayed directly onto the foliage of undesired plants. Irrigation water can provide a vehicle for herbicides in yet another mode of application.

The known methods of applying herbicides are disadvantageous because they require operations that are separate from the step of sowing the crop seed. For example, when herbicides are incorporated into the soil before the crop is seeded, application and tillage steps are employed. Treating weeds directly still involves the procedure of spraying the herbicide formulation onto the foliage thereof. Considerable expenditures of time, money, and energy, therefore, occur in conventional approaches to herbicide use.

SUMMARY OF THE INVENTION

I have found that the resources expended in prior methods of applying herbicides can be greatly reduced by the process of my invention. In accordance with the instant method herbicide and crop seed are introduced simultaneously into soil in close proximity to one another. Thus, a single operation results in both seed bed formation and herbicide application, this being the primary advantage of the present method. A further advantage of the invention is that the growth of undesirable plants is controlled or prevented in the precise area where such growth would be most detrimental, i.e., in the immediate area where the crop plants grow, without harmful action on crop seed or crop plants resulting from the germination of crop seed.

The success of my invention is quite surprising and unexpected. Application of herbicide together with crop seed as separate entities would be considered by those skilled in the art because the crop plants would be expected to be injured by high concentrations of herbicide in their immediate environment in the absence of substances which specifically antagonize any harmful action of the herbicide on the crop seed and the crop plants. Even greater likelihood of injury to crop plants would be anticipated if crop seeds were treated with herbicide prior to planting them. The so-treated seeds and resulting seedlings would be exposed to much higher concentrations of herbicide than in the above situation wherein seed and herbicide are separately placed in the soil at the same time in close proximity to one another.

I discovered, however, that crop seed and seedlings tolerate the high concentrations of herbicide associated with my method of application. Crop plants exhibit normal growth whereas weeds are controlled at a level of 85–100%, generally about 98–100% in the immediate area where crop plants grow.

DESCRIPTION OF THE PREFERRED EMBODIMENTS

As mentioned above, the benefits of the invention are achieved by introducing a herbicide into soil at the same time as and in close proximity to the seed being sown. Generally, the amount of herbicide employed and the amount of seed to be planted are determined by pilot trails.

Various methods of carrying out the process of the invention will be described next by way of illustration and not limitation. Other methods will, no doubt, be suggested to those skilled in the art with a knowledge of the principles of the instant invention which appear in this disclosure.

In one embodiment of the invention seed and herbicide, as separate entities, are placed together in seed rows or other seed beds. The herbicide can be applied in a liquid or solid state. Thus, a spray of herbicide dispersion or emulsion in water can be delivered to the seed row during the seeding operation. Alternatively, herbicide in the solid state or herbicide mixed with a carrier to render it solid can be employed in place of the liquid emulsion. Thus, powders can be prepared by mixing herbicides with conventional excipients, such as surfactants, fillers, and the like. Dust or particulate formulations can be obtained by absorbing herbicides onto or into solid carriers such as clay, vermiculite, attaclay, talc, and so forth.

In a preferred embodiment of the invention seed is treated directly with a herbicide. Such treatment can be achieved by absorbing the herbicide into the natural seed coat or into an artificial coating on the seed, by dispersing the herbicide on the surface of the seed, and the like. Attaching an artificial coating to seed, in general, is well known in the art and is carried out for a number of reasons. First of all, seeds are coated with an inert material in order to make their size uniform and thus facilitate accurate delivery from seeding apparatus. Secondly, the coating introduced onto the seed most often contains a fungicide to protect the seed and seedlings from destruction through fungal activity. In accordance with the invention herbicide can be incorporated into the coating applied to seeds, which are subsequently planted. Usually, the weight of coating applied to the seed is about 50 to 100% that of the seed itself. The amount of herbicide placed on the seed is dependent upon the amount of herbicide to be employed in the overall operation. Factors affecting the amount of herbicide used are the spacing of the seed in the seed row, the distance the herbicide is expected to spread from the seed, thus yielding a specific band of treatment, and the intensity of herbicidal control desired. A useful formula for determining the amount of herbicide to be placed on each seed is the following:

$$\frac{\text{Amount of herbicide}}{\text{seed}} =$$

$$\frac{\text{Amount of herbicide}}{\text{area}} \times \frac{\text{Spacing of seed per unit area in row}}{\text{seed}} \times \text{Width of band of treatment}$$

For example, to apply a particular herbicide, contained on the surface of the seed, at a rate of 1 kilogram per hectare, wherein the seeds are planted in a row with a spacing of 1 centimeter between seeds to obtain a treated band 5 cm wide, the amount of herbicide per seed would be $$\frac{1 \text{ kg}}{\text{hectare}} \times \frac{1 \text{ cm}}{\text{seed}} \times 5 \text{ cm} =$$

$$\frac{5 \text{ kg} \times \text{cm}^2}{\text{hectare} \times \text{seed}} \times \frac{1 \text{ hectare}}{10^8 \text{ cm}^2} = \frac{.05 \text{ mg}}{\text{seed}}$$

Seeds treated with herbicide are sown in a conventional manner. A particular advantage of this embodiment of the invention may be explained as follows. In some geographical locations two crops are planted in the same area. For example, alfalfa and rye seeds are co-planted in adjacent rows. However, the development of the alfalfa is retarded by competition from rye and from weeds. In accordance with the instant invention alfalfa seeds coated with an appropriate herbicide can be planted as above. A sufficient band of control of weed growth can be obtained in the immediate area of the alfalfa plants to allow both the alfalfa and rye crops to grow normally.

The invention is of broad utility and can be employed in the application of all types of herbicides both natural and synthetic, including those herbicides which interfere with the growth of undesirable plants without necessarily killing them. Herbicides that can spread from the area around the seed are especially suited to my method of application. The present method may be used in the planting of crop seeds of all kinds. By the term "crop seeds" is meant those seeds yielding plants which are grown and/or harvested for a specific purpose, such as profit making, and the like.

EXAMPLES

My invention is further demonstrated by the following illustrative examples. Herbicides were obtained from Stauffer Chemical Company, West Port, Connecticut.

EXAMPLE 1

In early December, barnyard grass seed was mixed into soil contained in flats in a greenhouse. Then, alfalfa seed and S-ethyl dipropylthiocarbamate (EPTC) were placed together manually in rows in the soil. EPTC was in the form of an 87.8% emulsifiable concentrate diluted with water. Ther rates of EPTC employed were 1.1, 2.2, and 3.4 kilograms per hectare (kg/ha). The extent of grass control and emergence of alfalfa plants was determined by counting at times appropriate for obtaining meaningful results during a four week period following planting. In addition, the vigor of the emerging alfalfa plants was evaluated by visual comparison of the treated and control (untreated) plants. The results are summarized below.

| Rate of EPTC (kg/ha) | Depth of planting (mm) | Control of grass (%) | Crop response Emergence (%) | Vigor (%) |
| --- | --- | --- | --- | --- |
| 0.0 | 16 | 0 | 61 | 100 |
| 1.1 | 16 | 93 | 62 | 100 |
| 2.2 | 16 | 100 | 61 | 95 |
| 3.4 | 16 | 100 | 57 | 90 |

EXAMPLE 2

Procedures similar to that described in Example 1 were followed in the field. In one experiment in early May foxtail millet seed was mixed with plot of soil. An appropriate quantity of 10% granular EPTC (attapulgite carrier) and 100 alfalfa seeds were placed together at a depth of 16 mm in a row 1 m in length. In another experiment in mid September Italian ryegrass seed was employed instead of foxtail millet seed. The depth of implantation of the alfalfa seed and EPTC was 13 mm. The results are tabularized below.

| Experiment | Rate of EPTC (kg/ha) | Depth of planting (mm) | Type of grass | Control of grass (%) | Width of band of control (cm) | Crop response Emergence (%) | Vigor (%) |
| --- | --- | --- | --- | --- | --- | --- | --- |
| May | 0.0 | 16 | millet | 0 | 0 | 8 | 100 |
| | 1.2 | 16 | millet | 100 | 5.0 | 19 | 96 |
| | 2.4 | 16 | millet | 100 | 6.0 | 24 | 91 |
| | 3.6 | 16 | millet | 100 | 7.0 | 8 | 87 |
| | 7.2 | 16 | millet | 100 | 6.5 | 16 | 76 |
| September | 0.0 | 13 | ryegrass | 0 | 0 | 42 | 100 |
| | 0.6 | 13 | ryegrass | 98 | 5.1 | 41 | 95 |
| | 1.2 | 13 | ryegrass | 100 | 6.2 | 33 | 80 |
| | 2.4 | 13 | ryegrass | 100 | 6.7 | 40 | 73 |

EXAMPLE 3

Clay granules of the same size and similar density as alfalfa seed were formulated to contain 10% EPTC. The so-prepared clay granules were mixed with alfalfa seed in a proportion that provided a rate of EPTC of 2.2 kg/ha. The mixture was sown in barnyard grass-infested soil with a tractor-mounted Planet Jr. seeder at three depths in late August. The responses of alfalfa and barnyard grass were evaluated as described in Example 1 for a period of five weeks after planting. The results are outlined below.

| Rate of EPTC (kg/ha) | Depth of planting (mm) | Type of grass | Control of grass (%) | Width of band of control (cm) | Crop response Emergence (%) | Vigor (%) |
| --- | --- | --- | --- | --- | --- | --- |
| 0 | 6 | Barnyard | 0 | 0 | 49 | 100 |
| 0 | 12 | Barnyard | 0 | 0 | 39 | 100 |

| Rate of EPTC (kg/ha) | Depth of planting (mm) | Type of grass | Control of grass (%) | Width of band of control (cm) | Crop Response Emergence (%) | Vigor (%) |
|---|---|---|---|---|---|---|
| 0 | 18 | Barnyard | 0 | 0 | 35 | 100 |
| 2.2 | 6 | Barnyard | 90 | 8.2 | 37 | 89 |
| 2.2 | 12 | Barnyard | 94 | 8.0 | 34 | 91 |
| 2.2 | 18 | Barnyard | 98 | 7.9 | 24 | 90 |

EXAMPLE 4

Two experiments were conducted in a greenhouse in December and January using barnyard grass as the undersirable plant species, which was mixed with soil. EPTC was applied to alfalfa seeds coated (50% of their weight) with a lime-based material (commercial product prepared by CelPril Corporation, Manteca, California). Using a micro syringe, a 1.0 microliter droplet of an acetone solution of technical grade EPTC was applied to each coated seed. The acetone evaporated within minutes, leaving EPTC on the seeds. Solutions of EPTC in acetone of 10%, 20%, and 40% provided the amount of EPTC required for rates of 2, 4, and 8 kg/ha, respectively, assuming the width of the band of treatment was 5 cm. The so-treated seeds were then spaced 1 cm apart in rows at a depth of 13 mm in the above soil. The responses of alfalfa and barnyard grass, measured during the four week period subsequent to planting, are summarized in the table below.

| Experiment | Rate of EPTC (kg/ha) | Depth of planting (mm) | Type of grass | Control of grass (%) | Width of band of control (cm) | Crop Response Emergence (%) | Vigor (%) |
|---|---|---|---|---|---|---|---|
| December | 0 | 13 | Barnyard | 0 | * | 73 | 100 |
|  | 2 | 13 | Barnyard | 91 | * | 77 | 100 |
|  | 4 | 13 | Barnyard | 97 | * | 70 | 88 |
| January | 0 | 13 | Barnyard | 0 | 0 | 77 | 100 |
|  | 2 | 13 | Barnyard | 66 | 5.1 | 78 | 100 |
|  | 4 | 13 | Barnyard | 97 | 8.3 | 70 | 90 |
|  | 8 | 13 | Barnyard | 100 | 9.9 | 68 | 85 |

*Not measured.

EXAMPLE 5

In a greenhouse different herbicides and crop seeds were applied in separate rows in soil seeded with barnyard grass. In each experiment untreated rows of each crop were paired with treated rows of that crop. The procedures employed were similar to those outlined in Example 1. Herbicides used were: (1) EPTC, (2) vernolate (S-propyl dipropylthiocarbamate, 10% granular formulation with attapulgite as a carrier), (3) cycloate (S-ethyl cyclohexylethylthiocarbamate, 75.2% emulsifiable concentrate in water), and (4) pebulate (S-propyl butylethylthiocarbamate, 75.2% emulsifiable concentrate in water).

Responses of the crops and barnyard grass were observed at appropriate times during the four week period following planting. The results are depicted in the table below.

| Crop | Herbicide Type | Rate (kg/ha) | Depth of planting (cm) | Control of grass in 5 cm band (%) | Width of band of grass control (cm) | Crop response Emergence (%) | Vigor (%) |
|---|---|---|---|---|---|---|---|
| Soybeans | None | — | 4 | 0 | — | 93 | 100 |
|  | EPTC | 3 | 4 | 100 | 10.0 | 77 | 70 |
|  | Vernolate | 3 | 4 | 99 | 10.0 | 87 | 85 |
| Field beans | None | — | 4 | 0 | — | 97 | 100 |
|  | EPTC | 3 | 4 | 100 | 10.0 | 97 | 100 |
|  | Vernolate | 3 | 4 | 97 | 10.0 | 100 | 100 |
| Alfalfa | None | — | 1 | 0 | — | 63 | 100 |
|  | EPTC | 3 | 1 | 100 | 10.0 | 56 | 85 |
|  | Vernolate | 3 | 1 | 100 | 10.3 | 63 | 93 |
| Turnip | None | — | 1 | 0 | — | 90 | 100 |
|  | EPTC | 3 | 1 | 100 | 10.1 | 90 | 87 |
| Sunflowers | None | — | 3 | 0 | — | 93 | 100 |
|  | EPTC | 3 | 3 | 96 | 10.5 | 93 | 93 |
| Flax | None | — | 2 | 0 | — | 63 | 100 |
|  | EPTC | 3 | 2 | 97 | 10.6 | 72 | 63 |
| Sugarbeet | None | — | 2 | 0 | — | 80 | 100 |
|  | Cycloate | 3 | 2 | 74 | 3.2 | 68 | 90 |
| Tomato | None | — | 1 | 0 | — | 73 | 100 |
|  | Pebulate | 3 | 1 | 64 | 2.0 | 84 | 97 |

EXAMPLE 6

In two separate experiments EPTC was applied directly to the seeds of field beans and sunflowers before the seeds were planted in barnyard grass seeded soil in a greenhouse. Using a micro syringe, a 3.0 microliter droplet of an acetone solution of technical grade EPTC was applied to each seed. The acetone evaporated within minutes, leaving the EPTC on the seeds. The so-treated seeds were then spaced 3 cm apart in rows at a depth of 3 cm in the soil. The solutions of EPTC in acetone at 10, 20, and 40% provided the amount of EPTC required for rates of 2, 4, and 8 kg/ha, assuming the width of the treated area was 5 cm. Sunflowers have a porous seed coat, which absorbed the herbicide solution immediately. The smooth, hard seed coat of the beans did not absorb the herbicide solution, but there was sufficient surface area on the large bean seeds to accommodate the droplet applied thereon.

Responses of the sunflowers, beans, and barnyard grass were determined at appropriate times for four weeks after planting. The results are outlined below.

| Crop | Rate of EPTC (kg/ha) | Depth of planting (cm) | Control of grass in 5 cm band (%) | Crop response Emergence (%) | Height (cm) | Vigor (%) |
|---|---|---|---|---|---|---|
| Sunflowers | 0 | 3 | 0 | 97 | 24 | 100 |
|  | 2 | 3 | 72 | 93 | 23 | 97 |
|  | 4 | 3 | 96 | 100 | 22 | 88 |
|  | 8 | 3 | 98 | 93 | 20 | 72 |
| Field beans | 0 | 3 | 0 | 80 | 20 | 100 |
|  | 2 | 3 | 19 | 73 | 20 | 100 |
|  | 4 | 3 | 40 | 73 | 20 | 100 |
|  | 8 | 3 | 77 | 83 | 20 | 96 |

Having thus described my invention, I claim:

1. A method of applying herbicide to control the growth of undesirable plants among crop plants, comprising
simultaneously introducing into the soil in close proximity, a crop seed and herbicide,
said herbicide having the capability of spreading from the area around the seed,
said herbicide being introduced in an amount sufficient, after spreading thereof, to control the growth of undesirable plants and insufficient to prevent an economically meaningful stand of said crop plants resulting from the germination of said crop seed,
said herbicide being introduced in an amount, before spreading, capable of causing injury to said crop resulting from germination of said crop seed,
said introduction being carried out in the absence of substances which specifically antagonize any harmful action of said herbicide on said crop seed and crop plants resulting from the germination of said crop seed.

2. The method of claim 1 wherein the amount of herbicide introduced is determined by the formula $$\frac{\text{amount of herbicide}}{\text{unit area of application}} = \frac{\text{amount of herbicide}}{\text{area}} \times \frac{\text{spacing of application}}{\text{unit area of application}} \times \text{width of desired band of treatment}$$

3. The method of claim 1 wherein said herbicide is in granular form.

4. The method of claim 3 wherein said herbicide in granular form is mixed with the crop seed prior to simultaneous introduction into the soil.

5. The method of claim 3 wherein said herbicide in granular form comprises an inert carrier of the size and density of the crop seed and formulated to contain said herbicide.

6. The method of claim 1 wherein said herbicide is in liquid form.

7. The method of claim 1 wherein said crop seed is treated with said herbicide, prior to introducing said seed into the soil.

8. The method of claim 7 wherein said seed is treated with herbicide by absorbing said herbicide into the natural coating of said seed.

9. The method of claim 7 wherein said seed is treated with herbicide by absorbing said herbicide into an artificial coating on said seed.

10. The process of claim 1 wherein said herbicide is an alkyl-substituted thiocarbamate.

11. The process of claim 1 wherein said crop seed is alfalfa seed.

12. The process of claim 1 wherein said crop seed is soybean seed.

13. The process of claim 1 wherein said crop seed is field bean seed.

14. The process of claim 1 wherein said crop seed is turnip seed.

15. The process of claim 1 wherein said crop seed is sunflower seed.

16. The process of claim 1 wherein said crop seed is flax seed.

17. The process of claim 1 wherein said crop seed is sugarbeet seed.

18. The process of claim 1 wherein said crop seed is tomato seed.

19. The method of claim 1 wherein said herbicide is s-ethyl dipropylthiocarbamate.

20. The method of claim 1 wherein said herbicide is s-ethyl dipropylthiocarbamate and said crop seed is alfalfa seed.

* * * * *